US009670432B2

(12) United States Patent
Heidari et al.

(10) Patent No.: US 9,670,432 B2
(45) Date of Patent: Jun. 6, 2017

(54) BIOLOGICAL METHOD FOR PREVENTING RANCIDITY, SPOILAGE AND INSTABILITY OF HYDROCARBON AND WATER EMULSIONS AND ALSO INCREASE THE LUBRICITY OF THE SAME

(71) Applicant: Saeed Mir Heidari, Irvine, CA (US)

(72) Inventors: Saeed Mir Heidari, Irvine, CA (US); Atefeh Ebrahimian Kafshae, Tehran (IR); Shahed Abbasi Soha, Tehran (IR)

(*) Notice: Subject to any disclaimer, the term of this patent is extended or adjusted under 35 U.S.C. 154(b) by 367 days.

(21) Appl. No.: 14/054,148

(22) Filed: Oct. 15, 2013

(65) Prior Publication Data
US 2014/0243248 A1  Aug. 28, 2014

(30) Foreign Application Priority Data
Feb. 24, 2013 (IR) .................. 13915014000309916

(51) Int. Cl.
*C10M 169/04* (2006.01)
*C07C 55/02* (2006.01)
*C10M 129/40* (2006.01)
*C10M 129/32* (2006.01)
*C10M 129/34* (2006.01)
*C10M 173/00* (2006.01)
*C10M 129/58* (2006.01)

(52) U.S. Cl.
CPC ........ *C10M 129/40* (2013.01); *C10M 129/32* (2013.01); *C10M 129/34* (2013.01); *C10M 129/58* (2013.01); *C10M 173/00* (2013.01); C10M 2207/122 (2013.01); C10M 2207/123 (2013.01); C10M 2207/126 (2013.01); C10M 2207/16 (2013.01); C10N 2210/01 (2013.01); C10N 2230/06 (2013.01); C10N 2230/16 (2013.01); C10N 2230/24 (2013.01); C10N 2250/02 (2013.01)

(58) Field of Classification Search
CPC ........................ C10M 2207/10; C10M 105/06
USPC ................................................. 508/220, 488
See application file for complete search history.

(56) References Cited

U.S. PATENT DOCUMENTS

| 1,533,158 | A | 4/1925 | Belknap |
| 1,830,969 | A | 11/1931 | Adams et al. |
| 2,423,619 | A | 7/1947 | Roon |
| 3,642,577 | A | 2/1972 | Gorring |
| 4,123,511 | A | 10/1978 | Heintze |
| 4,149,983 | A | 4/1979 | Grier et al. |
| 5,445,945 | A | 8/1995 | Drechsler |
| 6,921,745 | B2 | 7/2005 | Yamada et al. |
| 7,115,641 | B2 | 10/2006 | Merianos et al. |
| 7,439,376 | B2 | 10/2008 | Daly |
| 7,455,851 | B1 | 11/2008 | Nelson et al. |
| 7,595,288 | B2 | 9/2009 | Fretz et al. |
| 7,655,819 | B2 | 2/2010 | Daly |
| 7,989,405 | B2 | 8/2011 | Nettleship et al. |
| 2004/0087452 | A1* | 5/2004 | Noles ................... C10M 163/00 508/294 |
| 2008/0004177 | A1* | 1/2008 | Pfeiffer et al. ................ 504/100 |
| 2008/0292673 | A1* | 11/2008 | Crudden ................ A01N 25/12 424/417 |
| 2009/0029886 | A1* | 1/2009 | Chiba et al. ................... 508/283 |
| 2009/0324564 | A1* | 12/2009 | Maeda ....................... 424/93.47 |
| 2012/0167451 | A1 | 7/2012 | Festuccia |

FOREIGN PATENT DOCUMENTS

| CA | 1170247 | 7/1984 |
| EP | 0024146 | 2/1981 |
| EP | 0260863 | 3/1988 |
| EP | 1633190 | 3/2006 |

OTHER PUBLICATIONS

PCT, ISA/US, International Search Report and Written Opinion, May 14, 2014.
Ultan F Walsh, John P Morrissey and Fergal O'Gara, "Pseudomonas for biocontrol of phytopathogens: from functional genomics to commercial exploitation", Enviromental Biotechnology, 2001.
C.J. Van Der Gast, C.J. Knowles, M.A. Wright, I.P. Thompson, "Identification and characterisation of bacterial populations of an in-use metal-working fluid by phenotypic and genotypic methodology". 2001.
Yu-Huan Gu, Mark Mazzola, Impact of carbon starvation on stress resistance, survival in soil habitats and biocontrol ability of Pseudomonas putida strain 2C8; Soil Biology and Biochemistry Journal, 2011.
Robert F. Bonsall, David M. Weller and Linda S. Thomashow, Quantification of 2,4-Diacetylphloroglucinol Produced by Fluorescent *Pseudomonas* spp. In Vitro and in the Rhizosphere of Wheat; Applied and Environmental Microbiology Journal; Mar. 1997;.
T. Amein, Z. Omer, C. Welch, Application and evaluation of Pseudomonas strains for biocontrol of wheat seedling blight; Crop Protection Journal; 2008.).
Controlling sulphate reducing bacteria; Chem-Aqua journal; issue date: Dec. 19, 2006.
Monroe Don, Looking for Chinks in the Armor of Bacterial Biofilms. PLoS Biology (Nov. 13, 2007).
Heidi C. Sagen Wikmark, Co-existence of bacteria and filamentous fungi in experimental biofilms; 2008.
Cleide O. A. Møller, David Sabourin and Florian Berner, MicroSensor Measurement of Photosynthesis and Respiration in a Biofilm.
Lakshmiprasad Khochage; Rhamnolipid Biosurfactant from pseudomonas aeruginosa strains: screening, isolation and antimicrobial activity; May 2010.

(Continued)

*Primary Examiner* — Prem C Singh
*Assistant Examiner* — Francis C Campanell
(74) *Attorney, Agent, or Firm* — CIONCA Law Group P.C.; Marin Cionca

(57) ABSTRACT

A method for preventing degradation of physical and chemical properties, and for increasing lubricity, of a hydrocarbon and water emulsion, comprising adding to the emulsion an effective amount of at least one copper salt of a carboxylic acid for enabling at least one bacterium species from *Pseudomonas* genus to become dominant in the emulsion.

9 Claims, No Drawings

(56) References Cited

OTHER PUBLICATIONS

Carlos E. Rodrigues-Rodriguez, et al.; Evaluation of growth in diesel fuel and surfactants production ability by bacteria isolated from fuels in Costa Rica; RSVM journal.

Vidal, L., Thuault, V., Mangas, A., Covenas, R., Thienpont, A., Geffard, M. "Lauryl-poly-L-lysine: A New Antimicrobial Agent?" Journal of Amino Acids, vol. 2014, published Feb. 23, 2014; retrieved online Sep. 8, 2015.

Delihas, N., Riley, Loo, W., Berkowitz, J., Poltoratskaia, N. "High sensitivity of *Mycobacterium* species to the bactericidal activity by polylysine." FEMS Microbiology Letters, 233-237, published Oct. 1, 1995; retrieved online Sep. 8, 2015.

Tanaka, S., Hayashi, T., Tateyama, H., Matsumura, K., Hyon, S.H., Hirayama, F. "Application of the bactericidal activity of E-poly-L-lysine to the storage of human platelet concentrates." Transfusion. 50(4):932-40, published Nov. 20, 2009; retrieved online Sep. 8, 2015.

Ting, H.Y., Ishizaki, S., Tanaka, M. "Effect of the Maillard reaction on the bactericidal activity of e-polylysine." Journal of Tokyo University of Fisheries, vol. 84, No. 2, pp. 25-30, published Dec. 1997; retrieved online Oct. 2, 2015.

\* cited by examiner

BIOLOGICAL METHOD FOR PREVENTING RANCIDITY, SPOILAGE AND INSTABILITY OF HYDROCARBON AND WATER EMULSIONS AND ALSO INCREASE THE LUBRICITY OF THE SAME

CROSS-REFERENCE TO RELATED APPLICATIONS

This application claims priority to the foreign patent application no. 13915014000309916, filed in Iran on Feb. 24, 2013, which is hereby incorporated by reference, to the extent that it is not conflicting with the present application.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The invention relates generally to hydrocarbon and water emulsions and more particularly to a biological method for preventing rancidity, spoilage and instability of hydrocarbon and water emulsions and for increasing the lubricity of the same.

2. Description of the Related Art

Oil and water emulsions are used in many industries such as metal machining, textile, grease, metal forming, leather manufacturing, for various purposes such as cooling, lubricating, softening, corrosion protection, etc. The oil and water emulsions are an ideal place for microbial growth, which, if not prevented or controlled, causes the degradation of the emulsions, including making the emulsions useless.

In some industrial systems, such as the machines used in cutting metals, when the system shuts down and the emulsion circulation stops, the oxygen level in the emulsion declines and the resulting anaerobic environment promotes anaerobic bacterial growth and increase in $H_2S$ (hydrogen sulphide) gas which in turn causes an odor and reduction in the pH, and an eventual emulsion breakdown and separation of oil and water.

It is notable that the presence of fungi, yeast or mold, in the emulsions will result in a musty odor. Also, while, fungi usually do not affect the performance of the emulsions, in some cases a heavy fungal growth could result in blockage of parts, such as in fluid transfer pipes. In addition, the presence of fungi may have some harmful health effects on workers.

There has been considerable effort to improve emulsion formulations by making them bioresistant and by reducing the materials included in the formulations, which could be used as a food source by microbes. Some of the effort led to the use of a polymer with antimicrobial, bioresistant properties for metal working fluid and coatings. The bioresistant moiety that was linked into the backbone of the polymer is bromine/nitro group. In spite of all the effort and the solution provided (i.e., bioresistant polymer), there is still much microbial growth noticed in such fluids.

Furthermore, in many emulsions, there are ingredients such as hydrocarbons, surfactants, sulfur and phosphorous, which are suitable nutrients for microbial growth, and are thus biosupportive and not bioresistant ingredients. In some emulsions, the microbial growth could be so intense as to affect the physical and chemical properties of the emulsion, such as pH, rheological performance, emulsion stability, corrosion protection and odor, and even emulsion breakage resulting in the fluid becoming useless.

The level of destruction caused by the microorganisms depends on such factors as their type, population, the physical state of the system such as temperature, cleanliness, type of water used, and the age of the emulsion.

Other efforts led to the proposal of methods for preventing microbial contamination and degradation of emulsions, or other fluids containing biosupportive ingredients, by using biocides. For this purpose, a range of various chemical compounds are produced and used. Some of these biocides are compounds containing chemical entities such as halogens, organometallics, quaternary ammonium, phenols, metal salts, polycyclic amines, formaldehyde, and sulfur. Biocide performance is calculated in different manners, which include considering their effective concentration range (the optimum concentration for controlling the microbial growth) and their power of microorganism destruction which will determine the effectiveness of the remaining biocide in the environment. Other considerations are biocide's stability, physical properties, toxicity level, economics and environmental aspects.

Many biocides used in the industry at the present are either bactericide, fungicide or both and they can eliminate most and sometimes all of the microorganisms present in the targeted environment. These biocides could be part of the original formulation or could be added to the system continuously or periodically as needed.

A drawback of using biocide as a method for controlling microorganism growth in emulsions is the fact that microbes are present in most environments, such as air, water, soil and operators' hands and they continually contaminate the systems where the emulsions are used, and thus, the emulsions themselves. This causes the reduction and/or the elimination of the biocides in the respective emulsions, which, thus, require continual and/or periodical additions of biocides. Other drawbacks of biocides use are their adverse effects on the environment and workers' health. Another drawback is that microbes become resistant to the used biocide and thus the biocide has to be changed periodically.

It should also be noted that not all the microorganisms and in particular not all the bacteria in the nature are harmful towards emulsions and some of them would not change the chemical and the physical properties of such fluids. Contrarily, some of these bacteria promote the stability of the emulsion by secreting biosurfactant which helps in stabilizing the emulsion and some might have biocidal properties. Thus, killing all microorganisms by using biocides may be counterproductive.

Thus, as there is always a high potential for the hydrocarbon and water emulsions to be attacked by microorganisms, to make them spoiled and useless, there is a great need for a new and improved method that is effective and economical in protecting them from such attacks, and that addresses and solves the problems with the prior art described above.

The problems and the associated solutions presented in this section could be or could have been pursued, but they are not necessarily approaches that have been previously conceived or pursued. Therefore, unless otherwise indicated, it should not be assumed that any of the approaches presented in this section qualify as prior art merely by virtue of their presence in this section of the application.

BRIEF SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In one exemplary embodiment, a method is provided for preventing the hydrocarbon and water emulsions from becoming odorous, rancid, spoiled, unstable, or useless and for increasing the lubricity of the same. This is accomplished by using a certain fungicide and by providing a condition where a certain harmless bacterium grows and dominates the emulsions. Improvement in formulation of water and hydrocarbon emulsions by this method will reduce cost, improve performance of the emulsions, and prevent health related issues. More particularly, a non-exclusive list of advantages and benefits of the invented method is includes: prevention of spoilage and odor in oil and water emulsions; no need for periodical addition of biocide to the emulsion for duration of its use; no need for addition of harmful biocides to the emulsion; inhibition of growth of harmful and pathogenic microorganisms; ease of maintenance of the emulsion; decrease of the probability of pipes and passways to plug; increase of emulsion stability; increase of lubricity of the emulsion; suppression of anaerobic bacteria growth; improving stability in the pH of the emulsion; and, improving antioxidant properties of the emulsion.

The above embodiment(s) and advantages, as well as other embodiments and advantages, will become apparent from the ensuing description, and accompanying drawings if any.

DETAILED DESCRIPTION OF THE PREFERRED EMBODIMENTS

What follows is a detailed description of the preferred embodiments of the invention in which the invention may be practiced. The specific preferred embodiments of the invention, which will be described herein, are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

*Pseudomonas* species have been used effectively for biocontrol in agriculture. These species function in two ways in order to dominate the media: by secreting materials which have biocide properties; and by defeating the other competing microbes and reaching dominance by attaining most of the food source.

Aerobic bacteria such as strains of *Pseudomonas* genus commonly grow in oil and water emulsions in the presence of oxygen. These bacteria consume some materials present in the emulsion as their food.

In one aspect of the invention it was determined that *Pseudomonas* species, such as *Pseudomonas Pseudoalcaligenus, Pseudomonas Putida* and *Pseudomonas Fluorescens*, are more benign aerobic bacteria species, which do not harm the emulsions. Along with many other microorganisms (many of which could be harmful), these benign bacteria can grow in hydrocarbon emulsions, but they rarely ever become dominant. Thus, after finding the more benign aerobic bacteria species which do not harm the emulsions (i.e., *Pseudomonas* species, such as *Pseudomonas Pseudoalcaligenus, Pseudomonas Putida, Pseudomonas Fluorescens*, etc.), the associated challenge was to provide an environment where such benign bacteria species will flourish and dominate the emulsion.

Adding a fungicide to the emulsion could prevent the growth of fungi in the emulsion. However, while there are many fungicides which are used in different industries and products, almost all of them have bactericidal effects as well, which in this case would retard or stop the growth of the benign bacteria, the *Pseudomonas* species, such as *Pseudomonas pseudoalcaligenus Pseudomonas Putida, Pseudomonas Fluorescens*. Thus, efforts had to be made to identify a fungicide which will not negatively affect the growth of the mentioned benign *Pseudomonas* species. This was important, as again, the goal was to create the environment where the benign *Pseudomonas* species become dominant in the emulsion and thus can fulfill the biocontrol function in the emulsion. The efforts led to the discovery that copper salt of carboxylic acids, a fungicide used in agriculture, create the environment where the benign *Pseudomonas* species grow and become dominant in the emulsion, thus, preventing or significantly reducing the growth of other, harmful microbes. This is another aspect of the invention.

Thus, what is disclosed herein is a method for preventing the hydrocarbon and water emulsions from becoming odorous, rancid, spoiled, unstable, or useless, and for increasing the lubricity of the same. This is accomplished by using a carefully identified fungicide that provides a condition where a certain harmless bacterium grows and dominates the emulsions.

The fungicide is a copper salt of carboxylic acids, such as copper naphtenate, copper adipate or copper succinate, and preferably is a copper salt of fatty acids, such as copper caprylate, copper levirate, copper palmitate, copper stearate, copper oleate and copper cruciate. The fungicide may also be a mixture of copper salts of carboxylic acids.

The copper salts of carboxylic acids, in addition to having fungicidal properties, can improve oxidation, stability, lubricating and wear properties of the emulsion. The fungicide could be made in an emulsifiable form and used as a tank-side additive. The amount of fungicide (i.e., a copper salt of carboxylic acid or a mixture of copper salts of carboxylic acids) that may be added to the emulsion in order to achieve the results disclosed herein may be between 0.1 (zero point one) percent to 10 (ten) percent by weight.

Also, in addition to inhibiting fungal growth, the identified fungicide will also hinder the activity of anaerobic sulfur reducing bacteria, which are a main cause of spoilage and odor in oil and water emulsions. Laboratory observations appear to indicate that in the presence of copper salt of carboxylic acids, the activity of anaerobic bacteria declines. As known in the art, sulphate reducing bacteria use sulphates instead of oxygen for respiration and acquire their needed energy from oxidation of organic materials or hydrogen molecules during sulphate reduction to hydrogen sulphide. The formed hydrogen sulphide during respiration of these bacteria causes malodour and corrosion in the systems using the emulsion. Thus, using the identified fungicide helps prevent these undesirable results.

There is also a strong indication that, unlike the biocides commonly used in metal working fluids and other industrial emulsions, the identified fungicide does not have harmful health effects on, for example, the operators of machinery using such fluids and emulsions. It may be postulated that the NFPA (National Fire Protection Association) health rating of two copper salt of carboxylic acids (Copper Stearate and Copper Oleate) is about 2 to 3 times better than that of commonly used biocides.

Furthermore, because it is used in combination with the benign bacteria, as disclosed herein, the selected fungicide does not need to be added periodically or continuously to the emulsion, which is the case of the commonly used biocides. A one-time addition of the selected fungicide to the emulsion may be sufficient to create the environment where the selected benign bacteria become dominant, thus preventing the growth of other harmful microorganisms.

Again, the chosen dominant microorganism belongs to *Pseudomonas* genus which represents Gram-negative aerobic bacteria. In particular, it is one of the more harmless species, such as *Pseudomonas Pseudoalcaligenes*, *Pseudomonas Putida* and *Pseudomonas Fluorescens*. The chosen dominant species are capable of growing in harsh environmental conditions.

A beneficial characteristic of the selected bacterium is that it can secrete biosurfactants, which improve the emulsion stability. Starting with the known ability of the *Pseudomonas* strains to secrete biosurfactants, the biosurfactant secretion by the harmless *Pseudomonas* species and their effect on the pH increase and stability of emulsion was observed during the development of aspects of the invention, and was confirmed and tested as explained hereinafter.

A sample of emulsions of emulsifiable oil containing copper salt of carboxylic acids in water was made with an initial pH of 9.1 and RI (Refractive Index) reading of 5 showing an oil concentration of 5 (measured by a hand held refractometer). Diluted nitric acid was added to this sample to lower the pH to 7.40 and the sample was divided it in two new samples, 1 and 2. These two samples were left resting for 2 days and then they were sterilized to kill all the existing microorganisms. A cream like layer was noticed at the top of both samples which is sign of instability in the emulsions.

At this point, sample 1 was inoculated with *Pseudomonas Pseudoalcaligenes*, which resulted in microbial count of $10^3$ CFU/ml and a RI reading of 2.9 and pH of 7.4. Nothing was done to sample 2 which also showed a pH of 7.4 and RI reading of 2.9. Both samples were left into a shaker incubator for 10 days and then the pH and the RI of both samples where measured. The pH of the sample 1 was 8.76, its RI read was 4.8 and its microbial count was $10^7$ CFU/ml. Sample 2 had a pH of 7.45 and a RI reading of 2.9. The results of this test is postulated in the below table, clearly showing biosurfactant secretion by the microbes in the sample containing *Pseudomonas* species, resulting in a pH increase and oil reemulsifying back into the emulsion, and thus, an increased stability of the emulsion.

TABLE 1

| Sample | Initial Microbial Counts (CFU/ml) | Final Microbial Counts (CFU/ml) | Initial pH | Final pH | Initial RI | Final RI |
|---|---|---|---|---|---|---|
| 1 | $10^3$ | $10^7$ | 7.4 | 8.76 | 2.8-2.9 | 4.8 |
| 2 | 0 | 0 | 7.4 | 7.42 | 2.8-2.9 | 2.8-2.9 |

Another beneficial characteristic of the selected bacteria is that the biofilm produced is not considerable. For example, prior art data shows that *Pseudomonas Pseudoalcaligenes* produces a biofilm having an average thickness of only 0.50 µm, a maximum thickness of 10.45 µm and a biomass of only 0.62 $\mu m^3/\mu m^2$.

The low amount of biofilm improves inhibiting the growth of the undesired microorganisms, and also prevents the blockage of industrial systems. Reduction in biofilm formation further improves the stability of emulsion pH and its stability in general.

The low biofilm mass is very important for achieving the stability of the emulsions. As known in the art, biofilm formation causes anaerobic zones and provides suitable conditions for anaerobic bacteria growth. Thus, controlling the biofilm level helps control the growth of the anaerobic bacteria, which may be harmful to the emulsion. In addition, the formed biofilms are suitable zones for fungi growth. Also, usually, fungi, especially molds, grow more easily on areas where biofilm has been formed and use the bacteria biofilm as their food source. Thus, if the biofilm formation is minimized, the growth of fungi and other pollutants can be hindered as well.

Since the growth of fungi and anaerobic bacteria results in pH decrease and emulsion instability, biofilm reduction and consequent reduction of fungi and anaerobic bacteria growth will improve the emulsion stability and the stability of its pH levels.

Furthermore, formation of microbial mass as biofilm may plug pipes and reduce fluid flow. Thus, biofilm reduction will also help prevent these costly occurrences.

Thus, the inventive aspects are twofold: first, using a special fungicide which will create an environment where harmful microorganisms to the emulsion are reduced or eliminated and certain harmless and useful aerobic bacterium will grow to dominate the emulsion; secondly, adding some of the above-mentioned harmless and useful aerobic bacterium to the emulsifiable hydrocarbon concentrate to initiate and help the domination of such species in the emulsion.

Again, in order to prevent the growth of fungi and provide the suitable condition for growth of the dominant aerobic bacterium, a copper salt of carboxylic acid or a mixture of copper salts of carboxylic acids may be used. The copper salt of carboxylic acid(s) could be a specific molecule of copper and carboxylic acid or it could be a mixture of copper salts of various carboxylic acids, which could have a plant or animal source, such as castor oil, tall oil, lard oil or tallow oil. Using the selected fungicide promotes the growth and dominance of the selected benign bacterium by making the environmental condition difficult for other microorganisms to grow in the emulsion. Adding a specified amount of the desired bacterium as a preculture to emulsifiable oil concentrate helps the domination of this bacterium. The addition of the bacterium to the emulsifiable oil concentrate could be done as a preculture, in a dry (lyophilized) or liquid form.

It should be noted that the raw materials of the emulsifiable formulations can be further manipulated, so the desired bacterium would grow more easily and rapidly. There are many different ways and many different raw materials which could be used to emulsify organic materials in water. Depending on the desired properties of the emulsion for a particular use and the type of additives needed, one can select and manipulate the raw materials to get the desired properties, such as pH, hydrocarbon droplet size, emulsion stability and so on.

The amount of preculture added to base emulsifiable hydrocarbon depends on the level of bacteria counts in the preculture and could be between 0.01 to 10 percent, by weight.

The procedure for preparation of preculture and for adaptation of bacterium is fully described in microbiological and scientific references such as ASTM 2275-03.

It is noted that the beneficial results described herein regarding hydrocarbon and water emulsions may be also obtained by simply adding to the emulsion one or more of the copper salts of carboxylic acids described herein, so that an environment is created in the emulsion in which one or more of the benign *Pseudomonas* species may naturally grow and become dominant. Thus, the addition of *Pseudomonas* species to the emulsion may not always be necessary. It may just be optional, such as for aiding or expediting the natural growth and eventual dominance of the *Pseudomonas* species.

It may be advantageous to set forth definitions of certain words and phrases used in this patent document. A bioresistant material is one which, while it does not kill microorganisms, is not readily chemically decomposed by microbial attack. Simply put, a bioresistant material does not provide a ready food source for microorganisms. A biocide kills microorganisms.

The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

As used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims. Use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the embodiments and examples shown should be considered as exemplars, rather than limitations on the apparatus and procedures disclosed or claimed. Although many of the examples involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the described methods. Acts, elements and features discussed only in connection with one embodiment are not intended to be excluded from a similar role in other embodiments.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

Although specific embodiments have been illustrated and described herein for the purpose of disclosing the preferred embodiments, someone of ordinary skills in the art will easily detect alternate embodiments and/or equivalent variations, which may be capable of achieving the same results, and which may be substituted for the specific embodiments illustrated and described herein without departing from the scope of the invention. Therefore, the scope of this application is intended to cover alternate embodiments and/or equivalent variations of the specific embodiments illustrated and/or described herein. Hence, the scope of the invention is defined by the accompanying claims and their equivalents. Furthermore, each and every claim is incorporated as further disclosure into the specification and the claims are embodiment(s) of the invention.

What is claimed is:

1. A method for preventing degradation of physical and chemical properties, and for increasing lubricity, of an emulsifiable hydrocarbon or a hydrocarbon and water emulsion, comprising adding to the emulsifiable hydrocarbon or emulsion an effective amount of at least one copper salt of a carboxylic acid for enabling at least one bacterium species from *Pseudomonas* genus to become dominant therein, the method further comprising adding to the emulsifiable hydrocarbon or emulsion a bacterium species from *Pseudomonas* genus in order to aid the enabling of the at least one bacterium species from *Pseudomonas* genus to become dominant therein.

2. The method of claim 1, wherein the effective amount of the at least one copper salt of carboxylic acid is about 0.1 to 10 percent, by weight.

3. The method of claim 1, wherein the at least one copper salt of a carboxylic acid is from a group consisting of copper naphtenate, copper adipate and copper succinate.

4. The method of claim 1, wherein the at least one copper salt of a carboxylic acid is a copper salt of a fatty acid, which is from a group consisting of copper caprylate, copper levirate, copper palmitate, copper stearate, copper oleate and copper cruciate, and wherein the lubricity of the emulsion is increased by adding the copper salt of a fatty acid to the emulsion.

5. The method of claim 1, wherein the enabled at least one bacterium species is from a group consisting of *Pseudomonas Pseudoalcaligenes, Pseudomonas Fluorescens* and *Pseudomonas Putida*.

6. The method of claim 1, wherein the added bacterium species is from a group consisting of *Pseudomonas Pseudoalcaligenes, Pseudomonas Fluorescens* and *Pseudomonas Putida*.

7. The method of claim 1, wherein the added bacterium species is added to the emulsifiable hydrocarbon or the emulsion as a preculture amounting to about 0.01 to 10 percent, by weight.

8. The method of claim 1, wherein the at least one copper salt of a carboxylic acid is made emulsifiable and then added to in-use or ready-to-be-used emulsion, as an additive.

9. A method comprising creating of conditions for at least one bacterium species from *Pseudomonas* genus to become dominant in an emulsifiable hydrocarbon or hydrocarbon and water emulsion, said creating of conditions comprising adding to the emulsifiable hydrocarbon or the emulsion an effective amount of at least one copper salt of a carboxylic acid and a bacterium species from *Pseudomonas* genus, the method preventing degradation of physical and chemical properties of the emulsifiable hydrocarbon or hydrocarbon and water emulsion.

\* \* \* \* \*